United States Patent [19]

Sutherland et al.

[11] Patent Number: 5,025,787
[45] Date of Patent: Jun. 25, 1991

[54] INTRAUTERINE PROBE

[75] Inventors: Ian A. Sutherland, Harpenden; Nigel J. Randall, London; Philip J. Steer, Kingston upon Thames, all of England

[73] Assignee: The Imperial College of Science, Technology & Medicine, London, England

[21] Appl. No.: 484,956

[22] Filed: Feb. 26, 1990

Related U.S. Application Data

[63] Continuation-in-part of Ser. No. 330,020, Mar. 29, 1989, abandoned, and Ser. No. 346,971, Jun. 6, 1989, abandoned.

[30] Foreign Application Priority Data

Mar. 29, 1988 [GB] United Kingdom ............... 8807482
Oct. 8, 1989 [GB] United Kingdom ............... 8624169

[51] Int. Cl.$^5$ .............................................. A61B 5/04
[52] U.S. Cl. .................................. 128/642; 128/698; 128/748; 128/775
[58] Field of Search ............... 128/639, 642, 698, 748, 128/775

[56] References Cited

U.S. PATENT DOCUMENTS

| | | | |
|---|---|---|---|
| 3,326,207 | 6/1967 | Egan | 128/642 |
| 3,545,432 | 12/1970 | Berman | 128/640 |
| 3,572,322 | 3/1971 | Wade | 128/640 |
| 4,082,087 | 4/1978 | Howson | |
| 4,141,365 | 2/1979 | Fischell et al. | |
| 4,211,237 | 6/1980 | Nagel | 128/698 |

FOREIGN PATENT DOCUMENTS 0206248 12/1986 European Pat. Off.

Primary Examiner—William E. Kamm
Assistant Examiner—Kevin Pontius
Attorney, Agent, or Firm—Sughrue, Mion, Zinn, Macpeak & Seas

[57] ABSTRACT

A method of and apparatus for monitoring the condition of a fetus during labor includes an elongated flexible, flattened body member formed from an electrically insulating material having a rounded distal end and having at least oen sensor mounted in a flat face of the body member. The body member is sufficiently directionally stable to be insertable into the vaginal tract and through the cervix and is capable of being guided around the fetus without twisting. The body member has a bending stiffness about an axis transverse to the plane of the body member of between 1 and 10 mega-Newtons/m$^2$. Once the apparatus is introduced into the cervix, the signal ouptut from at least one electrode is analyzed by discriminating the fetal heart rate from the maternal heart rate.

17 Claims, 5 Drawing Sheets

TEMPORARY NOTICE of BEST AVAILABLE IMAGE

U. S. PATENT AND TRADEMARK OFFICE

THE SCANNED IMAGES OF PATENT NUMBER _5025787_ FOR THE ISSUE DATE OF _6/25/1991_ ARE NOT THE COMPLETE ORIGINAL DOCUMENT, BUT CONTAIN A COPY OF THE BEST AVAILABLE TEXT AND IMAGE DATA FROM VARIOUS SOURCES.

WHEN THE MISSING INFORMATION BECOMES AVAILABLE, THE DOCUMENT WILL BE RESCANNED AND REPLACED.

ANY QUESTIONS SHOULD BE DIRECTED TO THE DATA MAINTENANCE BRANCH BY TELEPHONE AT (703) 306-3116.

_DRew_
(Co Corrects)

TEMPORARY NOTICE of BEST AVAILABLE IMAGE

INTRAUTERINE PROBE

This application is a continuation-in-part of U.S. application Ser. Nos. 07/330,020 and 07/346,971 (corresponding to PCT/GB87/00713) filed on Mar. 29, 1989 and June 6, 1989, respectively, each now abandoned.

BACKGROUND OF THE INVENTION

This invention relates to an intrauterine probe which is suitable for use in monitoring conditions during labor, i.e. the condition of the fetus and also the condition of the mother.

The desirability of monitoring fetal heart rate (FHR) and intrauterine pressure (IUP) during a difficult labor is well known. In practice, IUP has been measured using a pressure catheter, and a separate device has been used to monitor FHR. Generally, FHR has been monitored by recording the voltage between two electrodes of which one is in the form of a body clip and the other (the "indifferent" or "reference" electrode) is spaced a short distance from the clip in contact with surrounding tissue (usually maternal).

The clip is attached to that part of the fetus which is presented for delivery. Normally, therefore, it is a scalp clip. A clip is necessarily invasive to the fetus, and is a disincentive to routine monitoring during labor. It is desirable clinically to carry out fetal monitoring routinely but this is unlikely to be achieved unless the procedure can be made more acceptable to women.

It would also be desirable to devise a system which would enable FHR and/or other factors to be monitored without the need to make separate trans-vaginal insertions.

SUMMARY OF THE INVENTION

The probe according to this invention is characterised by a flattened form which is floppy and comfortable enough to be inserted into the vaginal tract and through the cervical OS without discomfort, to take up a disposition where it lies alongside the fetus in utero, but at the same time, can be directed along a desired path and has sufficient transverse stiffness so as not to twist or turn over during or after insertion.

Electrodes for measuring the fetal heart rate (FHR) may be embedded in the body of the probe and in a preferred form, the surfaces of the electrodes lie approximately in the plane (or slightly below the plane) of one face of the body member of the probe. The probe may additionally or alternatively incorporate a sensor, e.g. a pressure sensor, so that the intrauterine pressure (IUP) can be monitored.

According to one aspect of the present invention there is provided an intrauterine probe for monitoring the condition of the fetus during labor which comprises an elongate flexible, flattened body member having a rounded distal end having at least one sensor mounted in each flat face of the body member, said body member being sufficiently directionally stable to be insertable into the vaginal tract and through the cervical OS and capable of being guided around the fetus without twisting.

Thus, for example, an electrode for detecting fetal heart rate (FHR) may be located in one face of the sensor, while an electrode located in the other face can be arranged to detect maternal heart rate (MHR). Because of the directional stability of the probe during and after insertion, it is a simple matter to ensure that the electrodes intended for detecting FHR will face the fetus, while the electrodes for detecting MHR will face away from the fetus. A predominate MHR signal will be detected by the electrodes facing away from the fetus and the wave form of this known MHR signal can be used to assist in discriminating the FHR from the mixed FHR and MHR signals picked up by the electrodes facing the fetus.

It may be advantageous to locate sensors for other parameters via the probe, either in addition to electrodes for detecting FHR and MHR or as an alternative. For example, it may be desirable to monitor maternal and fetal temperature. This can be done independently by locating fetal and maternal temperature sensors on opposite sides of the probe so that a temperature change in the mother or fetus can be rapidly detected independently. Alternatively, an optical sensor may be employed to detect, e.g. meconium and/or fetal blood oxygen levels when used as a trans-cutaneous oximeter. The probe may include one or more pressure transducers.

One of the underlying problems in using any intrauterine probe to monitor FHR is to distinguish fetal signals from maternal signals and from background noise. In the case of the prior art fetal scalp clips, it is hoped that the direct physical attachment will mean that the fetal signal "drowns" the maternal and background signals. Although close contact can be achieved to enhance signal detection, using the probe described in our application, we recognised that this was not essential for its operation. Because the amniotic fluid is an effective electrical conductor it can provide the necessary electrical path from the fetal skin to the electrodes. While this results in lower maternal and fetal signal levels they can be discriminated by 'R' wave width recognition using the signal processing technique described in detail below.

According to another aspect of the invention therefore there is provided an intrauterine probe for monitoring fetal heart rate (FHR) during labor which comprises an elongate flexible, generally floppy flattened body member formed from electrically insulating material and having a rounded distal end and at least two, longitudinally spaced electrodes located in one face or in opposite faces thereof, each electrode being located in a face of the body member so that at least one electrode can be pressed into close proximity with fetal skin. Preferably, the probe is designed so that there is a portion of insulating material between the electrodes whose profile is such that in use, a thin electrolyte film of amniotic fluid having a high impedance is present between the electrodes.

Improved signal detection is achieved by maximising the impedance between the 'active' electrode and the 'reference' electrode. Wide spacing of the reference and active electrodes along the length of the probe contributes to this end. However, the most effective measure to maximise impedance is to achieve a thin 'electrolyte' film of amniotic fluid between the electrodes, while ensuring that the electrodes are in fetal skin contact. If the probe profile which surrounds the electrodes has a generally flat top or slightly rounded shape (when seen in cross-section), a thin film thickness of the order of 0.5 mm or less may be achieved. Preferably, the upper surface of the electrode lies substantially in the same plane as the surface of the probe body. However, in a slightly less preferred embodiment the top surface of the electrode is located just beneath the plane of the probe surface.

From the standpoints of (FHR) measurements and uterocervical anatomy, the probe should satisfy certain criteria. The body of the probe is formed from an electrically non-conductive and non-toxic flexible material. It should be stiff/resilient enough to enable it to be inserted, by pushing from the proximal end through the cervix and around the fetal head. However, it should not be springY but sufficiently flexible and floppy so that it will lie along the surface of the fetus when inserted into the uterus.

The probe is generally flat in cross-section with rounded edges and with the electrodes located in the surface of one face. The flat sides enable the easy positioning of the electrodes, while fulfilling the requirement of surrounding the electrodes with insulating material. The shape also confers probe flexibility along the surface lying against the fetus, while providing sufficient transverse rigidity to allow the clinician to have control over the direction of insertion.

Details of construction and operation of intrauterine probes in accordance with the invention will be apparent from the following description and accompanying drawings in which.

Figure 1:
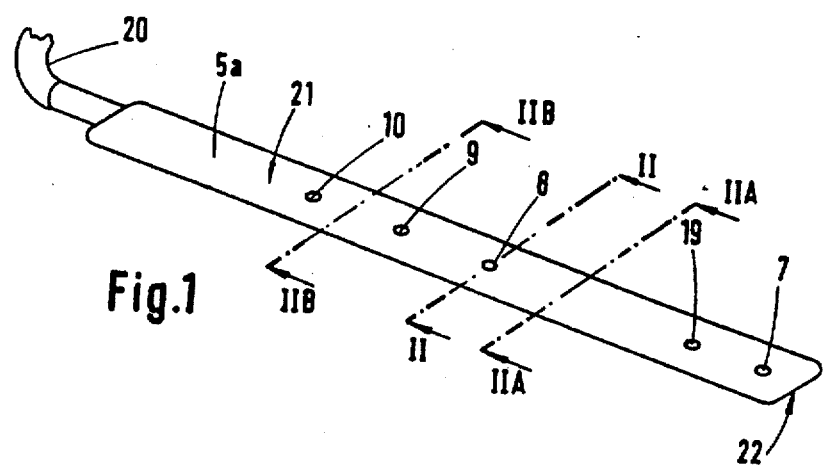
FIG. 1 is a perspective view of an embodiment of a probe in accordance with the invention.
Figure 2:
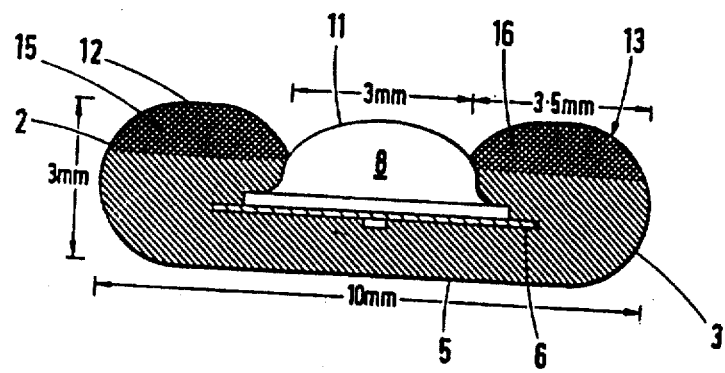
FIG. 2 is a cross-sectional view through an electrode of the probe of FIG. 1, taken on the line II—II.
Figure 2A:
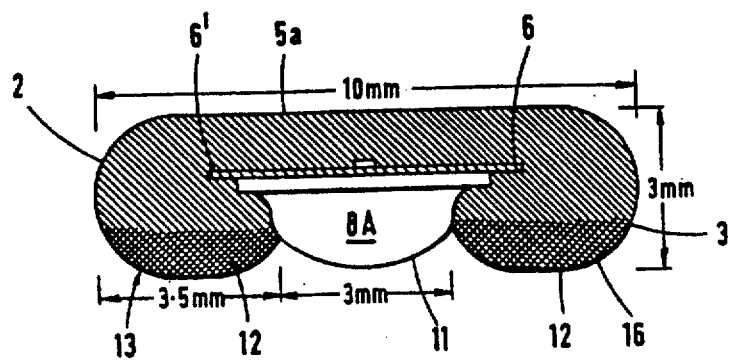
FIG. 2A is a cross-sectional view through the probe taken on the line IIA—IIA.
Figure 2B:
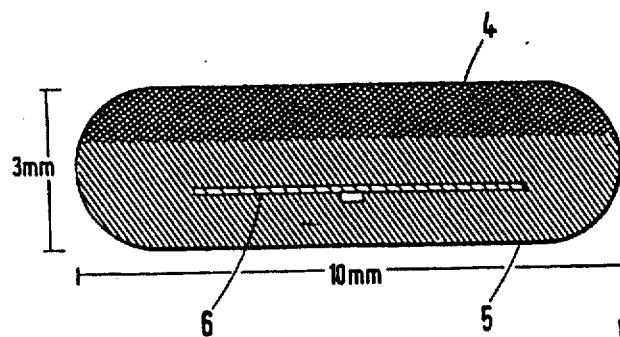
FIG. 2B is a cross-sectional view through the probe of FIG. 1, taken on the line IIB—IIB.

Referring to the drawings and in particular FIGS. 1, 2, 2A and 2B, the probe comprises an elongate body 1 about 40 to 50 cms in total length and having a rounded distal end 22. As best seen in FIGS. 2, 2A and 2B, the probe has a flattened configuration with rounded edges 2,3 and generally flat upper and lower faces 4, 5. Typically, the probe is about 1 to 2 cm wide and about 3 mm thick. A flexible printed circuit board 6 carries spaced electrodes e.g. of stainless steel 7, 8, 8A, 9 and 10 each having a domed head 11 and is encapsulated in a flexible plastics potting compound, such as a 2-part polyurethane composition. The dimensions and inherent flexibility of the plastics material are also such that the probe takes up the position shown in FIG. 3 when inserted in the uterus. The dimensions and inherent flexibility of the plastics material are such that when the probe is inserted into the uterus with one side facing the fetus, there is no tendency for the probe to twist. The particular potting composition employed was a 2-part polyurethane composition obtainable from Emerson & Cumming Ltd. 866 Uxbridge Road, Hayes, Middlesex, England, under the trade name CPC 19 flexible polyurethane potting compound or from Devcon under the trade name Devcon Flexane 80. Probes having a stiffness (Young's Modulus) in the range of 1 to 10 meganewtons per square meter are suitable.

As shown in FIG. 2, the domed head 11 of the electrode 8 is effectively shrouded by rounded portions 12 and 13 of the insulating material of the body. The surface of the domed portion 11 preferably lies substantially in the same plane as the flat face 5a of the body. In use, this ensures that amniotic fluid is squeezed out to form a thin electrolyte film between the electrode 8 and the reference electrode when the probe is suitably located in relation to the uterine or cervical walls.

FIG. 1 shows one surface of the probe, e.g. the surface which is intended to face the fetus. This surface may be marked, e.g., color-coded, so that the obstetrician can readily identify the side which is to be inserted so that it faces the fetus.

FIG. 2 shows a section through the probe of FIG. 1, which passes through the electrode 8 along the line II—II.

FIG. 2A shows a section through the probe along the line IIA—IIA. It will be apparent from FIG. 2A that the face 5 which cannot be seen in FIG. 1 is also provided with electrodes 8A. Electrodes 8A are similarly formed with domed portions 11 which preferably lie substantially in the same plane as flat face 5 of the body or slightly above or below. One or both faces 5 & 5A of the probe may have one or more electrodes and/or other sensors. In the case where the side 21 is intended in use to face the fetus, the electrodes 8A would be intended for measurement of MHR. Pressure sensor 19 may be located on either surface but may be more conveniently located on the surface which faces away from the fetus.

FIG. 2B shows a section between electrodes from which the encapsulated printed circuit board 6 can be seen.

As can be seen from FIG. 1, the electrodes are spaced so that the distal electrode 7 is spaced from the other electrodes 8, 8A, 9 & 10. As a consequence, the distance between electrode 7 and its nearest electrode 8A is greater than the inter-electrode spacing in the group of electrodes 8, 8A, 9 & 10. Because of its greater spacing the electrode 7 is generally used as the reference electrode. However, as will be described below, the signals detected by any pair of electrodes may be used for measuring the FHR. The spacing between electrode 7 and electrode 8A may typically be 8 to 12 cms, while the inter-electrode spacing in the group of electrodes 8, 8A, 9 & 10 may be, for example, 3 to 6 cms. As the birth progresses, the signals detected by each electrode may vary in strength and the signals may be processed by selecting, at any one time, the outputs from the pair of electrodes which give the best signal.

In contrast with the experience of scalp-clip monitors, the quality of the signals obtained from the probes of the invention often improve as the birth progresses. This is believed to be because the probe is pressed more firmly against the baby's neck as the fetal head passes into the birth canal.

Referring again to FIG. 2, the portion of insulating material surrounding the electrodes may be formed from a unicellular or closed cell foam. These portions 15 & 16 are shown in cross-hatching in FIGS. 2 & 2A. This may enable the probe to be pressed less tightly against the fetal skin while still minimising the effective 'electrolyte' film thickness.

Figure 3:
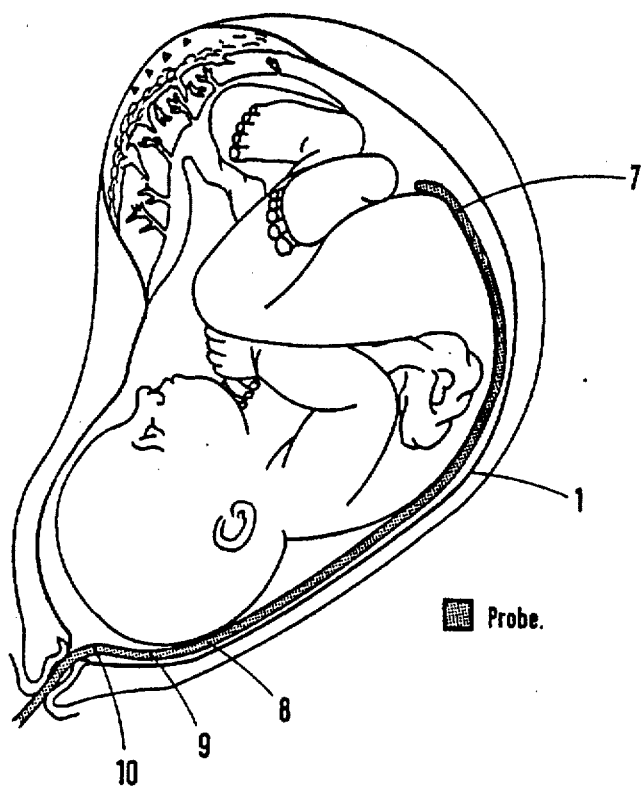
FIG. 3 is a schematic section of a uterus showing the probe in use.
Figure 4:
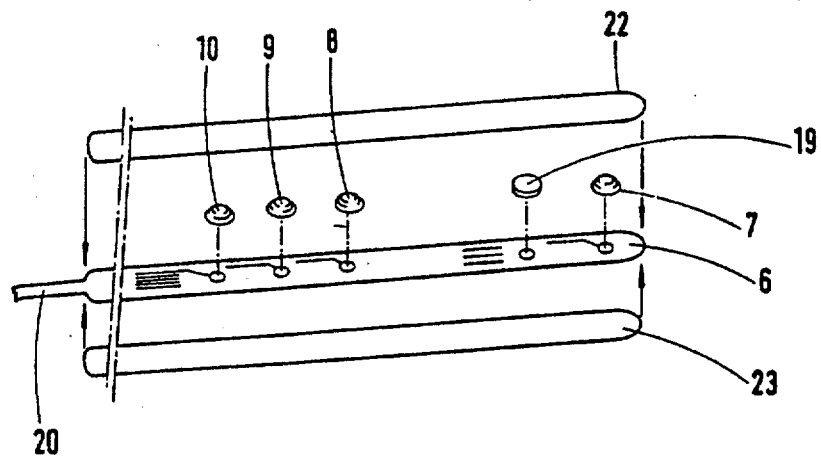
FIG. 4 is a diagrammatic exploded view illustrating one method of manufacturing a probe, in accordance with the invention in which the sensors are all located on one face of the probe.

Manufacture of a probe in accordance with the invention is illustrated in FIG. 3. This probe is the same as illustrated in FIGS. 1, 2, 2A & 2B, except that all of the electrodes are mounted on one face only of the probe. The electrodes 7, 8, 9 & 10 and also a pressure transducer 19 are attached to a printed circuit board 6. Board 6 includes conductor strips linking the electrodes to a multifilament cable 20 which is connected to a processor (see FIG. 6). Conveniently, the processor may include a digital display unit but may incorporate an oscilloscope and a chart recorder (not shown). Circuit board 6 and attached electrodes are encapsulated in a potting compound to form a shaped probe body having the general configuration shown in FIG. 1 by moulding between upper and lower moulds 22 & 23. A foaming agent may be introduced into the potting composition, or into a portion which will form the parts 16 & 17 of the probe body (see FIG. 2).

The minimum number of electrodes in the group 8, 9 & 10 is one but the more electrodes are present, the better the chance of maintaining good signal quality during birth. Generally 2 to 4 electrodes in the group are usually satisfactory. The group of electrodes are preferably spaced over a distance sufficient to encompass the fetal head and neck, e.g. at least about 5 cms, typically 5 to 15 cms. Interelectrode spacing is generally less than the distance between the electrode nearest the tip, i.e. electrode 8, and the distal electrode 7. This distance is commonly about 15 to 20 cms, e.g. about 18 cms. At present, the preferred configuration is a distal electrode 7 and three equally-spaced additional electrodes 8, 9 & 10.

In use, therefore, one at least of the group of electrodes 8, 9 & 10 is to a large extent redundant. At least one of the electrodes in the group will be useful, depending to some extent on the length of the fetus, and fetal movement after insertion. Sometimes two of the electrodes in the group will be utilised.

A probe of the invention can be used from the time at which the cervix is dilated to, say, 1 cm. The probe is inserted around the head or neck of the fetus and towards its lower trunk, and the flattened shape ensures that one face is stably oriented in contact with at least the head of the fetus. The intention is that the probe should be inserted to the extent that the distal electrode is on or adjacent to the lower trunk of the fetus, while one at least of the group of electrodes is in good contact with the head or neck of the fetus (see FIG. 3). At a later stage of labour to that shown in FIG. 3, the fetus' head and neck will be pressed against the electrodes 8, 9 & 10.

A probe of the invention in its preferred form includes a pressure sensor specifically to measure Intrauterine amniotic fluid Pressure (IUP). The location of this sensor is such that the point at which IUP is measured is both reasonably well known and unlikely to be influenced by unknown causes. By contrast with a pressure catheter, a pressure transducer and other sensors operating as miniature load cells (force sensors) for use in the invention can be constructed very cheaply.

Figure 5:
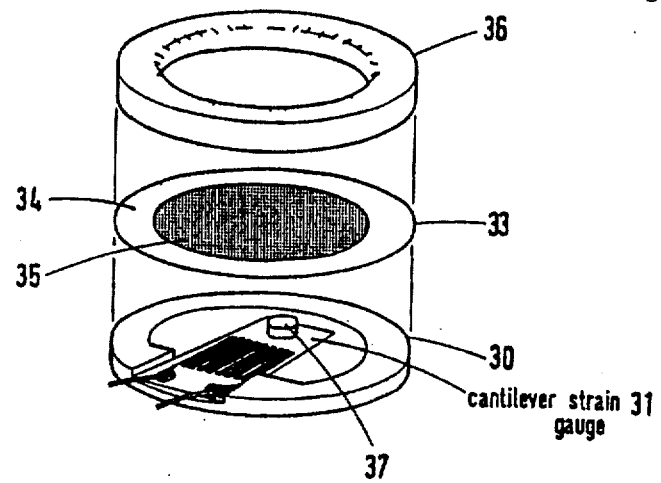
FIG. 5 is an exploded view of a pressure sensor on an enlarged scale.

Preferably the IUP sensor 19 is located at or close to the distal end of the probe. Its internal construction is shown in FIG. 5 and comprises a base carrier 30 which may be manufactured in metal (e.g. stainless steel), but is preferably moulded from plastics material (e.g. ABS plastic) and supporting a cantilever strain gauge (sensor) 31. The output from the strain sensor is connected to the printed circuit board 6. Overlying the base carrier is an assembly 33 comprising an annular thin film membrane 34 which supports a rigid plastics disc 35. The pressure sensor is completed by a sealing ring 36, which may be moulded in a rigid plastic e.g. ABS, or in a soft rubber-like material, over the base carrier and may include a grid structure to protect the membrane. In use, variations of IUP will cause the disc 35 to move inwardly and outwardly, thus applying more or less force to the strain gauge 31 via a contact button 37.

A probe of the invention provide a single device for the measurement of those criteria which are presently considered to be important for the good health of the mother and her baby. The probe can also be used, without changing its essential function, to measure further or different parameters; for example, there may be a temperature sensor which could be used to detect maternal hyperthermia or temperature variation during contraction, and/or an optical sensor which could be used to detect, say, meconium and/or fetal blood oxygen levels when used as a trans-cutaneous oximeter.

Figure 6:
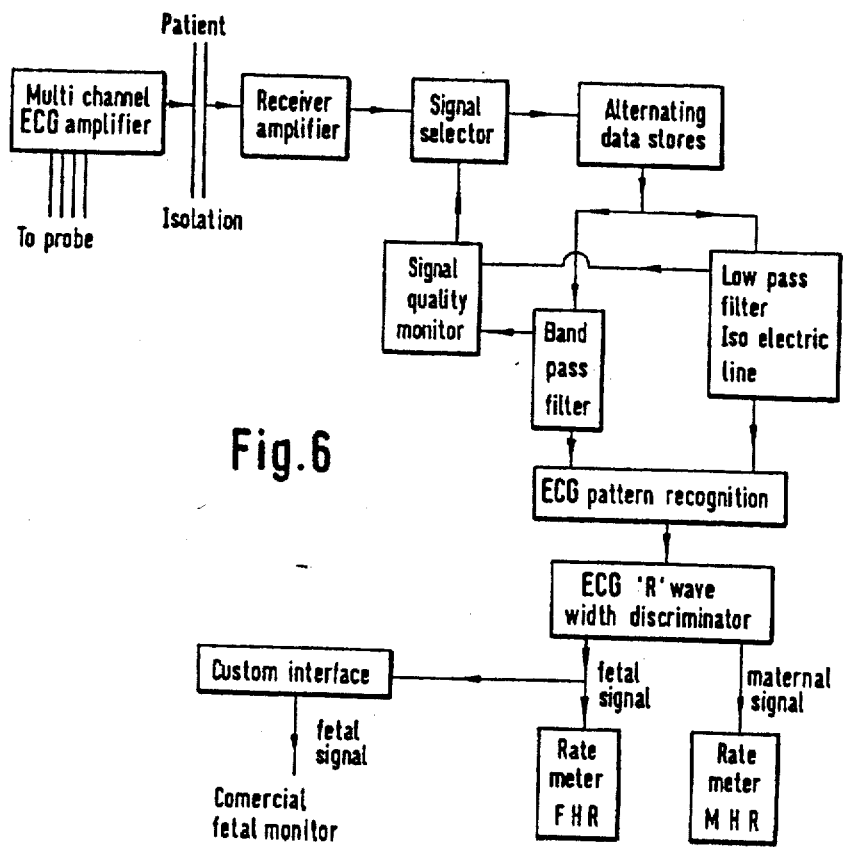
FIG. 6 is a schematic representation of the connection of the electrodes to a signal processor.
Figure 7:
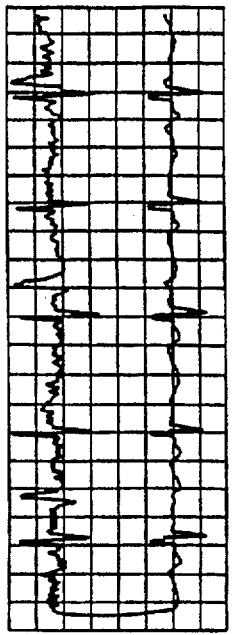
FIGS. 7a and 7b are a typical trace showing the fetal and maternal heart beats.
Figure 7:
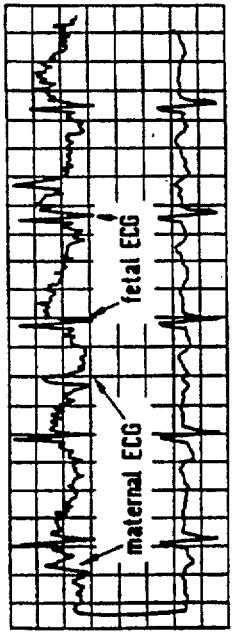

For use, a probe of the invention is connected with a processor and display means. An arrangement for processing and displaying the output from the probe is shown in FIG. 6. Typical traces produced by a chart recorder connected to a probe in accordance with the invention are shown in FIG. 7. The output from the electrode pairs is a mixture of maternal and fetal heart rates and background 'noise' deriving from other muscular activity. The specific processing to distinguish the maternal and fetal ECG complexes takes advantage of the differing morphologies of each. Results with the invention have demonstrated that the relative amplitudes of the fetal and maternal complexes during a given labour are unpredictable but the measured width of the fetal complex is consistently less than that of the maternal complex during the same labour. Hence, either frequency domain pattern recognition of the spectral components (amplitude and/or phase) after Fourier transformation of each complex, or temporal/spatial pattern recognition in real time and/or by retrospective analysis can be applied. Although the fetal heart rate signal cannot always be recognised uniquely by the measured width of its 'R' component, a combination of R wave width recognition in conjunction with comparison with a stored pattern can be used to separate unambiguously the fetal and maternal heart rates from each other and from background noise. In this way, those signals recorded by the electrodes processed in order to provide separate displays of FHR and MHR, together with the data obtained from the IUP sensor and other sensors at least. The display is visual, e.g. on a screen, but for the purposes of recording a chart recorder will be used (no other display may be necessary). Alternatively, the processed fetal heart signal and IUP can be made compatible with current commercial fetal monitors from which the FHR and IUP can be presented in the normal way.

FIG. 6 shows an arrangement in accordance with the invention for processing and displaying the signals detected by the probe.

Signals from the electrodes are fed to a multi-channel ECG amplifier and the amplifier output connected to the processing equipment via a patient isolation link such as a fibre optic cable. The transmitted signals are reamplified and then passed to a signal selector which monitors the signals and selects the best signals from any pair of electrodes. The selected signal is passed via a data store to a band width filter and a low pass filter (to establish the isoelectric line for the wave form). A feed-back to the signal selector is provided via a signal quality monitor to enable the signal selector to select signals on the basis of quality of fetal heart signal content as well as signal strength. After processing by an ECG pattern recognition unit, the signals are separated by an ECG R wave width discriminator into the fetal and maternal signals and the outputs displayed on rate meter display units, such as digital display units.

We claim:

1. An intrauterine probe for monitoring the condition of a fetus during labor, comprising:

an elongate flexible, flattened body member formed from electrically insulating material and having a rounded distal end, and having at least one sensor mounted in a flat face of the body member, said body member having a bending stiffness about an axis transverse to the plane of said body member of between 1 and 10 megaNewtons/m$^2$, whereby said body member is sufficiently directionally stable to be insertable into the vaginal tract and through the cervical OS and capable of being guided around the fetus without twisting.

2. A probe according to claim 1, including a distal sensor, and at least two additional sensors located in a group, wherein a spacing, lengthwise of said body member, between said distal sensor and the proximal additional sensors being greater than a spacing between said at least two additional sensors in the group.

3. A probe according to claim 2, wherein at least one of said sensors comprises an electrode for detecting fetal hear rate.

4. A probe according to claim 1, wherein said at least one sensor comprises a pressure transducer.

5. A probe according to claim 1, wherein portions of said electrically insulating material encircling said at least one sensor comprise a resilient foam material having non-communicating cells.

6. A probe according to claim 1, wherein portions of said electrically insulating material bounding said at least one sensor have a rounded upper surface in cross-section.

7. A probe according to claim 1, comprising at least two sensors spaced longitudinally thereof in at least one flat face of said body member.

8. A probe according to claim 7, wherein one of said at least two sensors comprises a distal sensor, said distal sensor being a pressure transducer.

9. A probe according to claim 1, wherein said electrically insulating material comprises polyurethane.

10. A probe according to claim 1, further comprising a processor, which is in structural communication with said at least one sensor, and which is adapted to distinguish between signals representing a fetal heart rate and a maternal heart rate.

11. An intrauterine probe for monitoring the condition of a fetus during labor, comprising:

an elongate flexible, flattened body member formed from electrically insulating material and having a rounded distal end, and at least one electrode located in one flat face of said body member; said body member having a bending stiffness about an axis transverse to the plane of said body member of between 1 and 10 megaNewtons/m$^2$, whereby said body member is sufficiently directionally stable to be insertable into the vaginal tract and through the cervical OS and capable of being guided around the fetus without twisting;

and said at least one electrode being mounted in said body member so as to be in close proximity to the fetal skin.

12. An intrauterine probe for monitoring fetal heart rate during labor, comprising:

an elongate flexible, flattened body member formed from electrically insulating material and having a rounded distal end, and at least first and second electrodes each of which are located in one flat face of the body member and being spaced longitudinally of; said body member having a bending stiffness about an axis transverse to the plane of said body member of between 1 and 10 megaNewtons/m$^2$, whereby said body member is sufficiently directionally stable to be insertable into the vaginal tract and through the cervical OS and capable of being guided around the fetus without twisting:

and each electrode being mounted in said body member so as to be in close proximity to the fetal skin.

13. A probe according to claim 3, wherein said first electrode is for detecting fetal heart rate and is located in one face of said body member, and said second electrode is for detecting maternal heart rate and is located in a second face of said body member.

14. A probe according to claim 13, further comprising a third reference electrode mounted in one face of said body member and spaced longitudinally of said body member from each of said first and second electrodes by a distance which is greater than a distance between said first and second electrodes.

15. A probe according to claim 12, including a plurality of electrodes in one flat face of said body member, said electrodes being spaced over a distance which, in use, is sufficient to encompass the fetal head, neck and back.

16. An intrauterine probe for monitoring fetal heart rate during labor, comprising:

an elongate flexible, flattened body member formed from electrically insulating material and having a rounded distal end; said body member having a bending stiffness about an axis transverse to the plane of said body member of between 1 and 10 megaNewtons/m$^2$, whereby said body member is sufficiently directionally stable to be insertable into the vaginal tract and through the cervical OS and capable of being guided around the fetus without twisting;

and at least two longitudinally spaced electrodes located in one face thereof, each electrode being mounted in said body member so as to be pressed into close proximity with fetal skin and having a portion of insulating material between said electrodes, said portion having a profile such that in use the amniotic fluid present between said electrodes is reduced to a thin electrolyte film having a high electrical impedance.

17. A method of monitoring fetal heart rate during labor, said method comprising the steps of:

introducing into the cervix a probe including an elongate, flexible, flattened body member formed from electrically insulating material; said body member having a bending stiffness about an axis transverse to the plane of said body member of between 1 and 10 megaNewtons/m$^2$, whereby said body member is sufficiently directionally stable to be insertable into the vaginal tract and through the cervical OS and capable of being guided around the fetus without twisting;

and having at least one electrode located in one face thereof; and analyzing the signal output from said at least one electrode by discriminating said fetal heart rate from a maternal heart rate based on at least one of a difference in ECG R wave signal width and frequency.

* * * * *

UNITED STATES PATENT AND TRADEMARK OFFICE
CERTIFICATE OF CORRECTION

PATENT NO. : 5,025,787

DATED : June 25, 1991

INVENTOR(S) : Sutherland et al

Page 1 of 7

It is certified that error appears in the above-identified patent and that said Letters Patent is hereby corrected as shown below:

The title page should be deleted to appear as per attached title page.

The Drawing sheets 1-5 should be added consisting of Figs. 1-7, as shown on the attached pages.

Signed and Sealed this

Twenty-fifth Day of May, 1993

Attest:

MICHAEL K. KIRK

Attesting Officer

Acting Commissioner of Patents and Trademarks

United States Patent [19]
Sutherland et al.

[11] Patent Number: 5,025,787
[45] Date of Patent: Jun. 25, 1991

[54] INTRAUTERINE PROBE

[75] Inventors: Ian A. Sutherland, Harpenden; Nigel J. Randall, London; Philip J. Steer, Kingston upon Thames, all of England

[73] Assignee: The Imperial College of Science, Technology & Medicine, London, England

[21] Appl. No.: 484,956

[22] Filed: Feb. 26, 1990

Related U.S. Application Data

[63] Continuation-in-part of Ser. No. 330,020, Mar. 29, 1989, abandoned, and Ser. No. 346,971, Jun. 6, 1989, abandoned.

[30] Foreign Application Priority Data

Mar. 29, 1988 [GB] United Kingdom ............ 8807482
Oct. 8, 1989 [GB] United Kingdom ............ 8624169

[51] Int. Cl.$^5$ ............................................. A61B 5/04
[52] U.S. Cl. ........................ 128/642; 128/698; 128/748; 128/775
[58] Field of Search .......... 128/639, 642, 698, 748, 128/775

[56] References Cited

U.S. PATENT DOCUMENTS

| | | | |
|---|---|---|---|
| 3,326,207 | 6/1967 | Egan | 128/642 |
| 3,545,432 | 12/1970 | Berman | 128/640 |
| 3,572,322 | 3/1971 | Wade | 128/640 |
| 4,082,087 | 4/1978 | Howson | |
| 4,141,365 | 2/1979 | Fischell et al. | |
| 4,211,237 | 6/1980 | Nagel | 128/698 |

FOREIGN PATENT DOCUMENTS 0206248 12/1986 European Pat. Off.

Primary Examiner—William E. Kamm
Assistant Examiner—Kevin Pontius
Attorney, Agent, or Firm—Sughrue, Mion, Zinn, Macpeak & Seas

[57] ABSTRACT

A method of and apparatus for monitoring the condition of a fetus during labor includes an elongated flexible, flattened body member formed from an electrically insulating material having a rounded distal end and having at least oen sensor mounted in a flat face of the body member. The body member is sufficiently directionally stable to be insertable into the vaginal tract and through the cervix and is capable of being guided around the fetus without twisting. The body member has a bending stiffness about an axis transverse to the plane of the body member of between 1 and 10 mega-Newtons/m$^2$. Once the apparatus is introduced into the cervix, the signal ouptut from at least one electrode is analyzed by discriminating the fetal heart rate from the maternal heart rate.

17 Claims, 5 Drawing Sheets

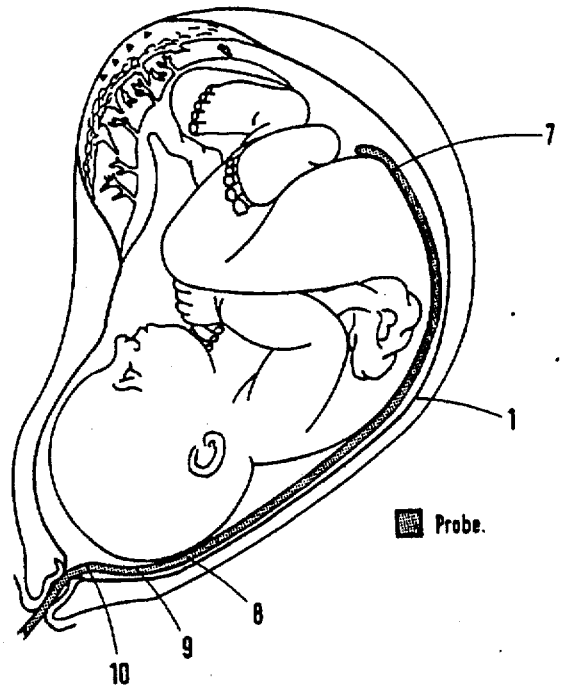

Patent No. 5,025,787

Typical signals from intra-uterine electrodes in accordance with invention. (upper trace)

maternal ECG
fetal ECG

Typical output from scalp-clip electrode. (lower trace)

Typical signals from intra-uterine electrodes in accordance with invention. (upper trace)

Typical output from scalp-clip electrode. (lower trace)